(12) United States Patent
Vinten-Johansen et al.

(10) Patent No.: US 6,900,008 B2
(45) Date of Patent: May 31, 2005

(54) METHODS AND FORMULATIONS FOR MINIMIZING SPASTICITY IN BLOOD VESSEL GRAFTS

(75) Inventors: Jakob Vinten-Johansen, Grayson, GA (US); Daniel A. Velez, Bothell, WA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 10/285,219

(22) Filed: Oct. 31, 2002

(65) Prior Publication Data

US 2003/0087878 A1 May 8, 2003

Related U.S. Application Data

(60) Provisional application No. 60/335,642, filed on Oct. 31, 2001, and provisional application No. 60/336,090, filed on Oct. 31, 2001.

(51) Int. Cl.[7] .............................................. A01N 1/00
(52) U.S. Cl. ...................................................... 435/1.1
(58) Field of Search ............................. 435/1.1, 1.2, 2

(56) References Cited

U.S. PATENT DOCUMENTS

| | | | | |
|---|---|---|---|---|
| 4,022,893 A | | 5/1977 | Moyer | 424/246 |
| 4,103,687 A | * | 8/1978 | Ishii | 604/500 |
| 4,250,191 A | | 2/1981 | Edwards | 424/308 |
| 4,361,564 A | | 11/1982 | Edwards | 424/250 |
| 4,532,135 A | | 7/1985 | Edwards | 514/222 |
| 5,898,035 A | | 4/1999 | Inchiosa et al. | 514/626 |
| 6,284,763 B1 | | 9/2001 | Adams et al. | 514/258 |

OTHER PUBLICATIONS

Tatoulis et al. "Bilateral radial artery grafts in coronary reconstruction: technique and early results in 261 patients", Annals or thoracic surgery 66 (3):714–19 (1998).*

Liu et al., "48–Hour Storage of Canine Kidneys after Brief Perfusion with Collins'Solution", Ann. Surg. 173(5): 748–757 (1971).*

Gryglewski et al., "Role of Endothelial Nitric Oxide in Pleiotropic Action of Cardiovascular Drugs: Nebivolo", IOS Press, 2001 Gryglewski et al. (Eds.), pp. 57–70.*

Harrison et al., Vasodilator pre–treatment of human radial arteries, European Heart Journal; vol 22, Issue 23, pp. 2209–2216, Dec. 2001.

Okon et al., Effect of Moderate Pressure Distension on the Human Saphenous Vein Vasomotor Function, The Annals of Thoracic Surgery, 77, pp. 108–115 (2004), Published by Elsevier Inc.

Daniel Velez, Cullen Morris, Satoshi Muraki, Jason Budde, Rachel Otto, Zhi–Qing Zhao, Robert Guyton, Jakon Vinten–Johansen, Brief Pretreatment of Radial Artery Conduits With Phenoxybenzamine Prevents Vasoconstriction Long Term, The Annals Of Thoracic Surgery, vol. 72, No. 6, (Oct., 2000), pp. 1977–1984.

Century of Advances—Abstract From the 72nd Scientific Sessions, Supplement to Circulation, Journal of the American Heart Association, vol. 100, No. 18, Section 3509 to 3514, Nov. 2, 1999.

M. A. Dipp, P.C. G. Nye, D. P. Taggart, Phenoxybenzamine is more effective and less harmful than papaverine in the prevention of radial artery vasospasm, European Journal of Cardio–Thoracic Surgery, vol. 19, pp. 482–486, Published 2001.

David P. Taggart, Michelle Dipp, Shafi Mussa, Piers Nye, Phenoxybenzamine Prevents Spasm In Radial Artery Condults For Coronary Artery Bypass Grafting, The Journal of Thoracic And Cardiovascular Surgery, vol. 120, No. 4, pp. 815–817, Published Apr. 20, 2000.

* cited by examiner

Primary Examiner—Sandra E. Saucier
(74) Attorney, Agent, or Firm—Norton & Diehl LLC; Scott S. Servilla

(57) ABSTRACT

The present invention relates to me methods for minimizing spasticity in blood vessels during transplantation and more particularly for minimizing spasticity in arterial transplants, for both ex-vivo and in-vivo procedures. The invention also relates to formulations, which can be used in these methods.

4 Claims, 10 Drawing Sheets

METHODS AND FORMULATIONS FOR MINIMIZING SPASTICITY IN BLOOD VESSEL GRAFTS

PRIORITY CLAIM

This application claims the benefit of the filing date of U.S. Provisional Patent Application No. 60/335,642 filed on Oct. 31, 2001, and U.S. Provisional Patent Application No. 60/336,090, filed on Oct. 31, 2001.

BACKGROUND OF THE INVENTION

1. Field of the Invention

The present invention relates generally to methods and formulations for minimizing spasticity in ex-vivo and in-vivo blood vessel grafts and more particularly to the minimization of spasticity though the administration of a spasticity minimizing agent solution to arterial grafts.

2. Description of the Background Art

As the patient population presenting with coronary artery disease (for example, but not limited to, those patients presenting with blocked coronary arteries) becomes older and 10% to 30% of these patients have to undergo cardiac re-operations involving replacement bypass grafts, there exists a need to identify new sources of bypass graft conduits and new treatments for the preparation of same.

Bypass graft conduits have traditionally been performed with venous grafts, typically pieces of veins from the patient's leg (generally the saphenous vein), which are harvested and then transplanted in a bypass procedure, typically a coronary bypass artery procedure. However, the use of arteries for bypass graft conduits has been increasing in frequency, these arteries generally having a more muscular media than that of veins and thus being able to withstand, on the average, higher blood pressures than that of venous grafts.

During the last 15 years, there as been a marked increase in the use of arterial conduits to perform coronary artery bypass grafting (CABG). The clinical and survival benefits of bilateral internal thoracic artery grafts have established them as conduits of first choice for CABG, whereas the radial artery has rapidly become the second most commonly used arterial conduit.

Blood vessel grafts, especially arterial grafts, commonly used in transplantations (bypass procedures) are prone to spasticity, i.e., vasospasm (the muscular media of the blood vessel wall having a tendency or increased tendency to undergo intermittent contraction) or "string sign" with use of vasopressor therapy both intra-operatively and post-operatively, and thus cause increased resistance and hence a decrease in blood flow through the arterial grafts. For example, the internal thoracic artery, like other arteries that are used for arterial grafts, has a capacity to undergo vasospasm or spasticity due to its inherent arterial nature of having more muscular media than venous blood vessels (veins). Such spasticity can result in a decrease in blood flow to the heart muscle resulting in angina, as well as possibly severe myocardial infarction or hypoperfusion. The spasticity of the artery can thus adversely affect the conduit's (graft's) long-term patency and can therefore result in the need to perform another coronary bypass procedure with a new graft or conduit within as few as three years. Specifically, radial artery bypass conduits are very prone to spasticity, causing increased resistance and decreased blood flow in coronary artery bypass grafts.

The radial artery is a versatile conduit, which can be harvested easily and safely, has handling characteristics superior to those of other arterial grafts, and comfortably reaches any coronary target. Several studies have reported superior patency of radial artery grafts compared with vein grafts at up to five years after CABG. Enthusiasm for widespread use of the radial artery as a conduit for CABG has, however, been tempered by its greater proclivity to spasm in the perioperative period.

Indeed, the radial artery was first suggested as a conduit (graft) for coronary artery surgery in 1973, but later was abandoned owing to a high failure rate (35% at two years post operation) of the graft, with such failures attributed primarily to vasospasm (spasticity). Later, the failure rate was reduced somewhat with the treatment of adding calcium-channel blockers and aspirin administered post-operatively. However, despite the use of the calcium-channel blockers, aspirin and vasodilators such as nitroglycerin, sodium nitroprusside and papaverine during the harvesting period of arterial grafts, vasospasm, hypoperfusion, and graft failure were still observed.

The tendency of the radial artery to spasticity (vasospasm) can thus result in severe post-operative myocardial hypoperfusion, as well as adversely affecting the grafts long-term patency. The capacity of the radial artery for vasospasm is several-fold greater than that of other arteries, for example the internal thoracic artery, because of its high muscular media and generally thicker arterial wall, and this spasticity/vasospasm risk is further increased in patients who require inotropic or vasoconstrictor therapy.

Various pharmacologic maneuvers have been recommended to reduce (minimize) the risk of radial artery vasospasm in the perioperative period, but all have significant limitations. Intravenous infusions of calcium channel blockers cause hypotension, bradycardia, and significant rhythm disturbances, whereas the topically applied agents, such as papaverine and nitroglycerin, have relatively short half-lives. The current pre and/or intra-operative treatment with papaverine, or other vasodilator agents, fails to either minimize, or provide a sustained inhibition of, spasticity (vasoconstriction) during and immediately after transplantation.

Thus, arterial grafts, and most particularly radial arterial grafts, have a greater tendency to spasticity or vasospasm due in part to the greater muscularity of arteries as compared to veins. For radial arteries, the increase of musculature in the arterial wall, the thicker media and a more dense organization of myocytes and less connective tissue than other arteries, such as the internal mammary artery, all combine to make the radial artery more susceptible to vasoactive substances, for example potassium, serotonin, and the alpha agonists norepinephrine and phenylephrine. As a result, arterial grafts, and radial artery grafts in particular, are at a greater risk for spasticity (vasospasm) during catecholamine surges that occur during cardiopulmonary bypass and post-surgical events (such as discontinuation of ventilation and removal of chest tubes) as well as during the administration of pressor agents to sustain the patient's blood pressure during the post-operative period.

Presently, phosphodiesterase inhibitors, which are vasodilator agents, such as papaverine, are used to reduce spasticity (i.e., attenuate or minimize vasospasm) of arterial grafts. However, papaverine treatments are also problematic in that they are limited by the temporary reduction in constrictor responses and seem to result in an overwhelmingly high risk of endothelial damage of the prospective arterial graft segments.

Finally, the problems of a greater tendency to spasticity or vasospasm and short term patency in internal thoracic arterial grafts has minimized the use of said artery in coronary bypass grafting and essentially mandated the use of ex-vivo procedures for coronary bypass grafting using harvested arterial grafts. Ex-vivo procedures for such harvested arterial grafts typically require the artery to be harvested to be removed from the body of a donor or patient and placed into a sterile environment, cooled down for transport of the artery from the operating room to a laboratory or other room (if attempts to minimize spasticity are performed), and thereafter warmed up again to approximately body temperature, while being provided with oxygen and maintained at proper pH (typically around pH 7.4) for transportation back to the operating room and implantation back into the body of the patient. The time requirements for such ex-vivo methods, in addition to sterility, oxygenation and cold/heat shock concerns to the harvested arterial graft, can be serious drawbacks and at the very least delay the transplantation or implantation of the harvested artery in a coronary bypass procedure.

SUMMARY OF THE INVENTION

We have surprisingly discovered that use of a spasticity minimizing agent, for example an haloalkylamine alpha-adrenergic antagonist (blocking agent), such as phenoxybenzamine, in solution applied topically, in a soaking solution bath or infused into a blood vessel graft attenuates (i.e., reduces) spasticity or vasoconstriction induced by inotropic agents such as phenyleprine or norepineprine for up to and including 48 hours post treatment (harvesting of a blood vessel and implantation of said harvested blood vessel graft) by ex-vivo procedures and in-vivo procedures. In the in-vivo procedure, the internal thoracic artery is not removed from the patient, but instead is harvested (cut) at only one location (end) and thus, while the internal thoracic artery is still part of the patient's circulatory system, the harvested end of the internal thoracic artery can be treated immediately if desired on-site (for example in the operating room) with an infusion of, or soak with, a phenoxybenzamine solution or other alpha-adrenergic solution, and then the detached harvested end of the internal thoracic artery is attached and implanted to connect with the blocked coronary artery.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

The harvesting of the blood vessel to be grafted may be performed on both veins and arteries, with arteries being harvested to form arterial grafts being preferred.

Any artery may be harvested to use in the procedure discussed herein, including but not limited to the internal mammary (thoracic) artery, the gastroepiploic artery, the inferior epigastric and radial artery, with radial arteries being harvested to form radial arterial grafts in an ex-vivo procedure, and the internal thoracic artery being harvested to form an internal thoracic arterial graft in an in-vivo procedure, being preferred.

Figure 1:
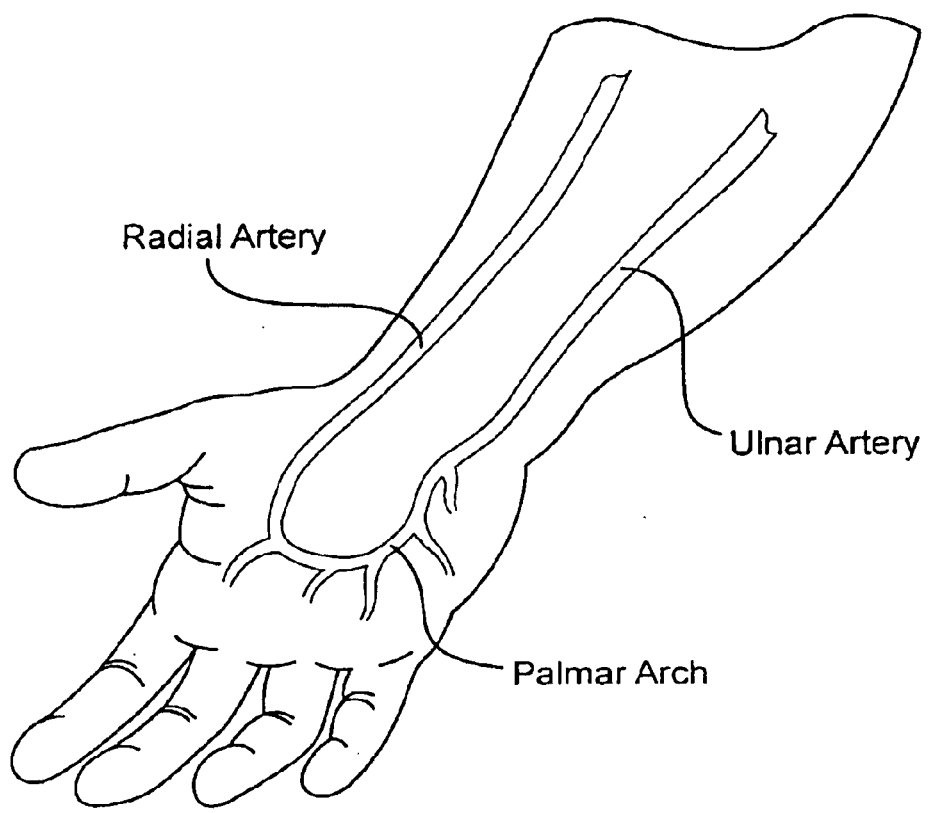
FIG. 1 depicts the location of the radial artery in the arm, wrist and hand area with a notation as to how the artery is completely removed from the body, and then pretreated ex-vivo in a solution prior to being transplanted back into the body to connect into an obstructed coronary artery distal to (below) the obstruction.

The harvesting procedure is performed according to methods well known in the art, but preferably is performed to harvest either the artery as a skeletonized vessel, without any surrounding connective tissue (pedicle) (See, for example. FIG. 1), or as a direct harvest of the artery with the surrounding connective tissues (pedicle) (See, for example, FIG. 2). Optimally, due to known surgical concerns regarding harvesting (such as, for example, the one touch issue), the harvesting procedure is a direct harvest of the radial artery and surrounding pedicle for the ex-vivo procedure. For the in-vivo procedure, the internal thoracic is harvested from the chest wall, its distal end is detached (cut) and used to connect with the obstructed coronary artery below the obstruction.

In one method of harvesting the radial artery, a fasciotomy of the radial artery with pedicle is performed to expose the arterial vessel wall to a spasticity minimizing agent, preferably a solution comprising, in whole or in part, a spasticity minimizing agent, for example phenoxybenzamine. The spasticity minimizing agent solution may optionally be combined with at least one vasodilator agent and an anti-coagulating agent to form a spasticity minimizing agent pretreatment solution, such as for example a phenoxybenzamine pretreatment solution, as a pharmaceutical formulation. In this method, the pedicle of the radial artery is incised longitudinally overlying the radial artery, as well as the underlying fascia overtop of the radial artery. This particular method permits direct exposure of the wall of the radial artery to the spasticity minimizing agent pretreatment solution, for example the phenoxybenzamine pretreatment solution, while also permitting the radial artery to partially extend and thus either reach more, or be utilized in, longer grafts.

Following the harvesting of the blood vessel to be grafted, the harvested blood vessel is soaked in the solution comprising the spasticity minimizing agent, for example phenoxybenzamine, or the pretreatment solution, for a period of time, preferably about 5 to about 60 minutes. The soaking step is performed as per known methods in the art, and includes direct perfusion, injection into the lumen of the vessel, pressurized intralumenal injection, and other well-known techniques. For example, the soaking step may be performed through intralumenal injection of the solution comprising the spasticity minimizing agent, for example phenoxybenzamine, into the lumen of an artery, such as the lumen of the radial artery, with subsequent clamping of one or both ends of the artery to retain the solution comprising the spasticity minimizing agent (for example phenoxybenzamine) intralumenally.

Alternatively, the soaking step may be carried out through the indirect exposure of the vaso vasorum, using direction of the spasticity minimizing agent solution, for example a phenoxybenzamine pretreatment solution, into accompanying and parallel veins. The pretreatment solution may optionally include an amount of the patient's blood and further may also include a physiologic crystalloid buffer solution. In this soaking step, one end of the artery, with pedicle, is clamped (including the artery and veins), while the veins are individually injected with some pressure about 0.01 mm Hg to about 100 mm Hg to perfuse the wall of the artery.

In another embodiment of the soaking step, the harvested radial artery itself can be directly perfused, as mentioned herein, with pressure controlled to about 0.01 to about 100 mmHG, to permit direct perfusion of the vaso vasorum branches coming off the radial artery lumen.

In yet another embodiment of the soaking step, pressure is utilized to assist the penetration of the solution of the spasticity minimizing agent, for example phenoxybenzamine (i.e. a phenoxybenzamine pretreatment solution), into the artery, such as the radial artery, and pedicle. In such a procedure, the harvested artery is placed into an enclosure, such as a cup, and the solution of the spasticity minimizing agent (phenoxybenzamine) is added. The enclosure is then enclosed and pressurized at about 0.01 mm Hg to about 100 mm Hg to force the solution of the spasticity minimizing agent (phenoxybenzamine), as well as associated medications, such as antibiotics, anesthetics or other known medications typically utilized in such a bypass procedure, if desired, into the wall of the artery.

In addition, the pharmaceutical formulation for minimizing (i.e., reducing or attenuating) spasticity in blood vessels ("soaking solution") may be used in accordance with the present invention for any intracoronary or intravascular introduction such as intralumenal injection into the internal thoracic artery, as well as in peripheral vascular implants or conduits, for example fem-popliteal bypasses or shunts, in minimizing spasticity in cerebral vessels, for example repair of aneurysms, occlusion of A-V fistulae by external or endovascular approaches, in minimizing spasticity during re-vascularization of free-flaps, in brachial or other artery shunts for vascular access in dialysis patients, in repair or re-vascularization of amputations or other traumatic repairs (for example, but not limited to, re-anastomosis of torn vessels for digital or limb reattachment after traumatic amputation or trauma resulting from, for example, gunshots and sharp or blunt trauma), as well as normal exposure techniques known to those skilled in the art, for example but not limited to fasciotomy, infusion via the companion veins, intralumenal exposure and intralumenal pressurization to penetrate via the blood vessel (for example, the vaso vasorum). The "soaking solution" can also be used via local delivery into organs, tissues or tissue layers either by itself, or as a co-infusate of agents to minimize or inhibit spasticity as either a primary effect or part of a side effect.

The soaking step can also be performed through the introduction of the solution of the spasticity minimizing agent, or the pretreatment solution, such as for example the phenoxybenzamine pretreatment solution, intracoronarily or intravascularly, for example intracoronary introduction of the of the solution of the spasticity minimizing agent such as phenoxybenzamine into a vaso-spastic coronary artery or into an arterial graft already in place to reduce or minimize spasticity (vasospasm). In one embodiment of this procedure, the arterial vessel or graft undergoing spasticity (the spastic graft) can be catheterized under fluoroscopy and the solution of the spasticity minimizing agent such as phenoxybenzamine then infused. In such a procedure, a catheter may be used to also temporarily occlude the vessel or graft distally, causing a graft space, with the solution of the spasticity minimizing agent such as phenoxybenzamine then added to fill and soak ("dwell") within the graft space for a given period of time. The solution of the spasticity minimizing agent such as phenoxybenzamine could then be either allowed to flush into the circulation upon removal of the catheter occlusion or can be re-aspirated through the coronary catheter to avoid systemic circulation. Those skilled in the art will appreciate the ability of this procedure to be applied to any other organ, such as but not limited to the kidney, brain, peripheral skeletal muscles, etc.

The spasticity minimizing agent of the present invention is selected from the group consisting of haloalkylamine alpha adrenergic blocking agents, and preferably is selected from the group consisting of phenoxybenzamine, isomers of phenoxybenzamine and tertiary amines of phenoxybenzamine.

The spasticity minimizing agent may be diluted into a solution, the solution of the spasticity minimizing agent, in a concentration of about $10^{-6}$M to about $10^{-1}$M. The diluent may be selected from the group consisting of normal saline and related physiological solutions and buffer solutions known in the art. Additionally and preferably, for a pharmaceutical formulation, the solution of the spasticity minimizing agent is combined with at least one vasodilator agent, such as for example lidocaine, xylocaine, tetracaine, procaine and other short-term vasodilators such as papaverine, adenosine, nitric oxide donor agents, calcium channel blocker agents, sodium channel blocker agents and related adenosine regulating agents, and an anti-coagulating agent to form a spasticity minimizing agent pretreatment solution, such as for example heparin, coumadin, ETDA, citrate, EGTA and other anti-coagulating agents that increase activated clotting time greater than about 200 seconds, to form the pretreatment solution of the spasticity minimizing agent. The at least one vasodilator agent is present in a concentration of about 5 to about 60 mg, and preferably is selected from the group of lidocaine and papaverine, while the anti-coagulating agent is present in a concentration of about 10 to about 1000 IU or approximately the concentration sufficient to make activated clotting time, the time in which clotting will begin to activate or start, greater than about 200 seconds.

The use of the spasticity minimizing pretreatment solution, such as the phenoxybenzamine solution, was demonstrated to be statistically significant in reducing (i.e., attenuating or minimizing vasospasm or spasticity) in the following experiment examples conducted with harvested canine radial arteries (Example 1) and human radial arteries (Example 2).

EXAMPLE 1

Canine radial arteries were harvested without pedicles, and incubated in control buffer or solutions of papavarine ($10^{-6}$M), 2, 3-butadione monoxime (BDM, $10^{-6}$M) (a putative protein phosphatase) or phenoxybenzamine ($10^{-6}$M) for a period of 30 minutes. The arteries were then washed with buffer and stored in a drug-free culture medium for a set time period (2 hours, 24 hours or 48 hours per example). After storage, vasopressors norepinephrine or phenylephrine were added at incremental concentrations ranging from 0.7 to 3.5 $\mu$mol/L (norepinephrine) or 0.300 to 1.5 $\mu$mol/L (phenylephrine) to all arterial samples to attempt to induce spasticity or vasoconstriction. The degree of vasoconstriction was then quantified in organ chambers. The responses of the arterial samples to norepinephrine or phenylephrine were compared with spasticity or constriction with receptor-independent potassium chloride (KCl) at 30 mmol/L.

In control radial artery segments the concentration-dependent contractile responses to norepinephrine and phenylephrine were not significantly different at any concentration after 2 hours, 24 hours, and 48 hours of storage. The maximum responses of untreated and treated radial artery segments of KCl, phenylephrine and norepinephrine (in grams of tension) are summarized in Table 1. The constriction (contraction) responses to phenylephrine and norepinephrine given below are represented as a percentage of the responses to KCl, i.e. 100×(grams tension norepinephrine/grams tension KCl).

The maximal constriction (contraction) response to norepinephrine was observed at 3.5 $\mu$mol/L, and averaged 54%±2% at 2 hours, 54%±3% at 24 hours, and 58%±7% at 48 hours relative to contractile responses to KCl. Phenylephrine-induced constrictor responses followed a similar concentration-dependent contractile pattern with the maximum contractile response being observed at 1.5 $\mu$mol/L. There were no significant differences in contractile responses at any concentration of phenylephrine between 2 hours, 24 hours, and 48 hours of storage; maximum contraction responses (% of KCl-induced response) averaged 67%±4% at 2 hours, 62%±6% at 24 hours, and 65%±6% of KCl response at 48 hours.

TABLE 1

Contraction Responses to Norepinephrine and Phenylephrine from Resting Force (approx. 3 g tension for each subset) in Untreated and Treated Radial Artery Segments

|  | 2 Hours | 24 Hours | 48 Hours |
| --- | --- | --- | --- |
| Norepinephrine |  |  |  |
| Control | 7.48 ± 1.23 | 6.22 ± 0.48 | 5.14 ± 0.55 |
| Pxb (phenoxy-benzamine) | 0.80 ± 0.05[b] | −0.58 ± 0.05[b] | −1.62 ± 0.36[b] |
| Pap (papaverine) | 7.65 ± 0.72 | 10.37 ± 0.26 | 12.55 ± 1.22 |
| BDM (2,3-butadionemonoxime) | 5.69 ± 0.29 | 4.22 ± 0.75 | 7.01 ± 0.85 |
| Phenylephrine |  |  |  |
| Control | 10.62 ± 0.57 | 10.14 ± 0.64 | 7.13 ± 0.85 |
| Pxb | 2.03 ± 0.13[b] | 0.20 ± 0.01[b] | −1.08 ± 0.19[b] |
| Pap | 14.29 ± 0.76 | 12.33 ± 0.76 | 10.46 ± 0.52 |
| BDM | 8.35 ± 0.79 | 9.43 ± 0.64 | 7.01 ± 0.80 |

[b]$p < 0.05$ versus paired control radial segments.

There was no significant attenuation (minimization) of vasoconstrictor responses to either norepinephrine or phenylephrine 2 hours, 24 hours, or 48 hours after pretreatment with the vasodilator papaverine versus untreated arteries. Interestingly, there was a paradoxical trend toward increased maximal constrictor response to both norepinephrine and phenylephrine in papaverine-treated radial artery rings at 48 hours of storage compared with the respective control vessels. However, this increased constrictor response did not reach significance. There was no significant difference in maximum constriction relative to KCl responses in the control vessels with 3.5 $\mu$mol/L norepinephrine (54%±2% at 2 hours, 53%±1.0% at 24 hours, and 58%±7.2% at 48 hours) or 1.5 $\mu$mol/L phenylephrine (67.0%±3.5% at 2 hours, 62.0%±1.6% at 24 hours, and 65.2%±5.7% at 48 hours) that might have accounted for these apparent increased responses to either vasoconstrictor in the papaverine-treated vessels. Therefore papaverine had no inhibitory effect on norepinephrine or phenylephrine-induced contraction after washing (2 hours) or after 24 or 48 hours after the 30-minute pretreatment.

Maximal constriction responses to norepinephrine in radial artery segments pretreated with BDM were significantly greater compared with the respective control vessels at 2 hours (approximately 50% for the control and approximately 75% for BDM treated segments). However, after 24 hours and 48 hours of drug-free storage, constriction responses to norepinephrine were similar between control vessels and drug-tested vessels. Constrictor responses of BDM-treated radial artery segments exposed to phenylephrine were very similar to control segments at 2 hours and 24 hours but were significantly attenuated only after 48 hours of storage (approximately 65% for the control and approximately 39% for the BDM treated segments).

However, the application of norepinephrine in phenoxybenzamine-treated radial artery segments did not increase constriction, but rather at all concentrations of norepinephrine utilized, constriction was attenuated in phenoxybenzamine-treated segments compared with untreated segments. Pretreatment of the radial artery segments with 1×$10^{-6}$M phenoxybenzamine for 30 minutes significantly attenuated constrictor responses to the maximum concentration of norepinephrine and phenylephrine at all three time points as shown in FIG. 3A–F. Two hours after exposure to phenoxybenzamine, constrictor responses to the entire range of concentrations of norepinephrine were significantly inhibited, with the maximal constriction response averaging −7%±1% of KCl response compared with 49%±2% in untreated vessels. Significant inhibition of maximal constrictor responses were still observed 24 hours (−5%±5% versus 42%±3%) and 48 hours (−20%±5% versus 58%±7%) after treatment with phenoxybenzamine versus untreated vessels, respectively. In addition, constriction responses to phenylephrine were also significantly attenuated (i.e., reduced) in vessels pretreated with phenoxybenzamine with constriction response to the maximum concentration of phenylephrine significantly lower 2 hours after treatment versus untreated vessels (19%±8% versus 67±4) see FIG. 3A–F. This attenuation or minimization was sustained and even enhanced at 24 hours (1%±4% versus 62%±2%) and 48 hours (−12%±4% versus 65%±6%) after a 30 minute pretreatment with phenoxybenzamine, respectively.

EXAMPLE 2

Inhibition of Alpha Agonist-induced Vasoconstriction by Phenoxybenzamine in Human Radial Arteries Radial artery (RA) segments were obtained from patients having elective coronary artery bypass grafting with or without cardiopulmonary bypass at the Crawford Long Hospital of Emory University. A modified Allen's test was performed to assess the adequacy of collateral circulation to the hand preoperatively. The RA was harvested with its pedicle containing the venae comitantes, perivascular fat and areolar tissue (no fasciotomy) using a "no-touch" technique. Branches of the RA were ligated with vascular clips. A subset of the radial artery grafts had the musculofascial tissue incised (with fasciotomy) to expose the aerolar tissue adjacent to the graft. The RA was then placed in a solution containing 20 mL heparinized blood, 1.6 mL 1% lidocaine and 0.4 mL papaverine (30 mg/mL) for approximately 30 minutes. The RA graft was flushed intraluminally with the blood/papaverine/lidocaine solution at the beginning and after 15 minutes of the soaking period. Prior to its placement in the aortocoronary position, a small segment of the RA was obtained and immediately placed in Krebs-Henseleit (K-H) buffer (118 mmol/L NaCl, 4.7 mmol/L KCl, 1.2 mmol/L $KH_2PO_4$, 1.2 mmol/L $MgSO_4$, 2.5 mmol/L $CaCl_2$, 12.5 mmol/L $NaHCO_3$, and 10 mmol/L glucose) at 4° C., pH 7.4 and transported to the Cardiothoracic Research Laboratory.

The harvested radial artery segment with or without fasciotomy was placed into K-H buffer pH 7.4 with either 10, 100 or 1000 $\mu$M PBZ or vehicle. The radial artery was flushed intraluminally twice with this solution, once at the beginning and once at the end of a 30 minute incubation period, which approximates the time between RA harvest and placement in the aortocoronary position. In addition, Control RA segments were obtained prior to intraoperative pretreatment of the conduit with the papaverine/lidocaine solution and received no other treatment. The segments were prepared for placement in organ chambers by carefully skeletonizing them in cold K-H buffer and cutting them into rings three to five mm in length. The rings were then mounted on stainless steel hooks, connected to FT-03 force displacement transducers, and placed into Radnoti organ chambers (Radnoti Glass, Monrovia, Calif. containing 7 mL of oxygenated (95% $O_2$, 5% $CO_2$) K-H buffer at 37° C. and pH 7.4. Indomethacin (10 $\mu$mol/L) was added to the buffer to block responses to endogenous prostanoids. The rings were stabilized for one hour with frequent buffer changes and set to a predetermined tension that allowed 75% of maximal contraction to 30 mM potassium chloride (KCl).

The rings were then incubated with increasing concentrations of PE (0.5 to 15 $\mu$M) or NE (0.5 to 15 $\mu$M). After the highest concentration of alpha adrenergic agent was achieved, 30 mM KCl was added to the bath to quantify the maximal nonreceptor-mediated constriction. In randomly selected vessels, the integrity of the radial artery endothelium was also tested for its receptor-dependent relaxation response to incremental concentrations of acetylcholine (ACh), a stimulator of nitric oxide synthase. The rings were precontracted with the thromboxane A2 mimetic U46619 (1.4 nmol/L), and then exposed to increasing concentrations of Ach (1 nmol/L to 11.7 $\mu$mol/L) in the presence of 10 $\mu$M indomethacin.

The changes in isometric force were quantified using an analog-to-digital converter sampling at 2 Hz. The responses were analyzed using a Windows-based videographics program (SPECTRUM, Wake Forest University, Winston-Salem, N.C.). The force of contraction elicited by the exposure to increasing concentrations of PE and NE was expressed as a percentage of the maximal contraction generated by KCl in each ring. The degree of relaxation after exposure to ACh was expressed as the percent tension reduction from the maximal force of contraction obtained from U46619.

Data were analyzed for significance using a one-way analysis of various (ANOVA) comparing the control, papaverine/lidocaine and phenoxybenzamine (PBZ) groups at each concentration of norepinephrine and phenylephrine. If a significant difference between groups was assigned by ANOVA, a post-hoc Student-Newman-Keuls test was applied to locate the source of differences. A p value of <0.05 was considered to be statistically significant. All data are reported as means±the standard error of the mean.

Figure 4:
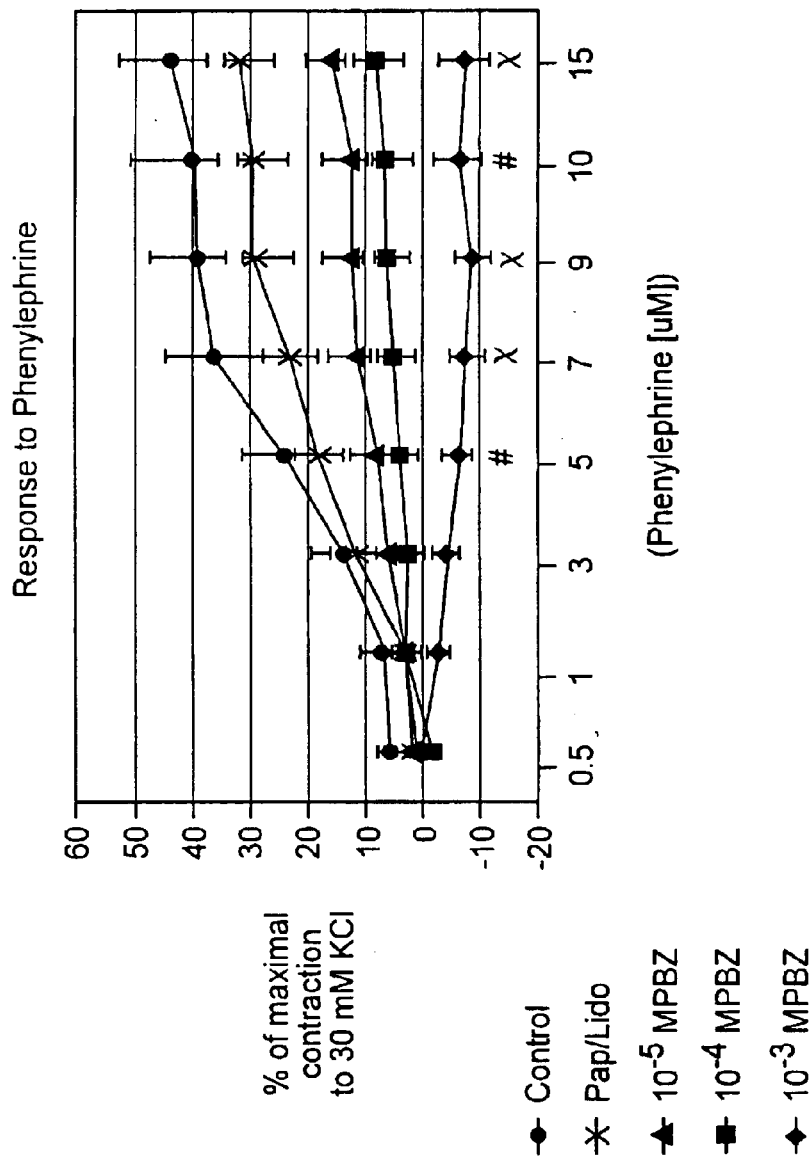
FIG. 4 depicts human radial artery vasocontraction responses to increasing concentrations of phenylephrine, with or without pretreatment with three different concentrations of phenoxybenzamine (PBZ)

Application of phenylephrine (PE) caused a concentration-dependent vasoconstriction in Control radial artery segments; the contraction achieved at the maximal concentration of PE (15 $\mu$M) averaged 44.2±9.1% of the KCl response (FIG. 4). Pretreatment of the radial artery in papaverine/lidocaine solution did not significantly attenuate the concentration-dependent contraction responses to PE. Contraction at the highest concentration of PE was reduced by only 27% of control vessels (32.1±5.9%, p=0.22 vs. Controls). In contrast, PBZ in addition to papaverine/lidocaine attenuated (reduced) the vasoconstriction to PE in a dose-dependent manner (FIG. 4). At the highest concentration of PE used (15 $\mu$M), the vasoconstriction response was attenuated (i.e., minimized) by 63% of control at 10 $\mu$M PBZ (16.5±4.3%, p=0.02), by 80% of control at 100 $\mu$M PBZ (8.7±5.1%, p=0.003) and by 116% of control at 1000 $\mu$M PBZ (−7.2±4.4%, p<0.001).

Figure 5:
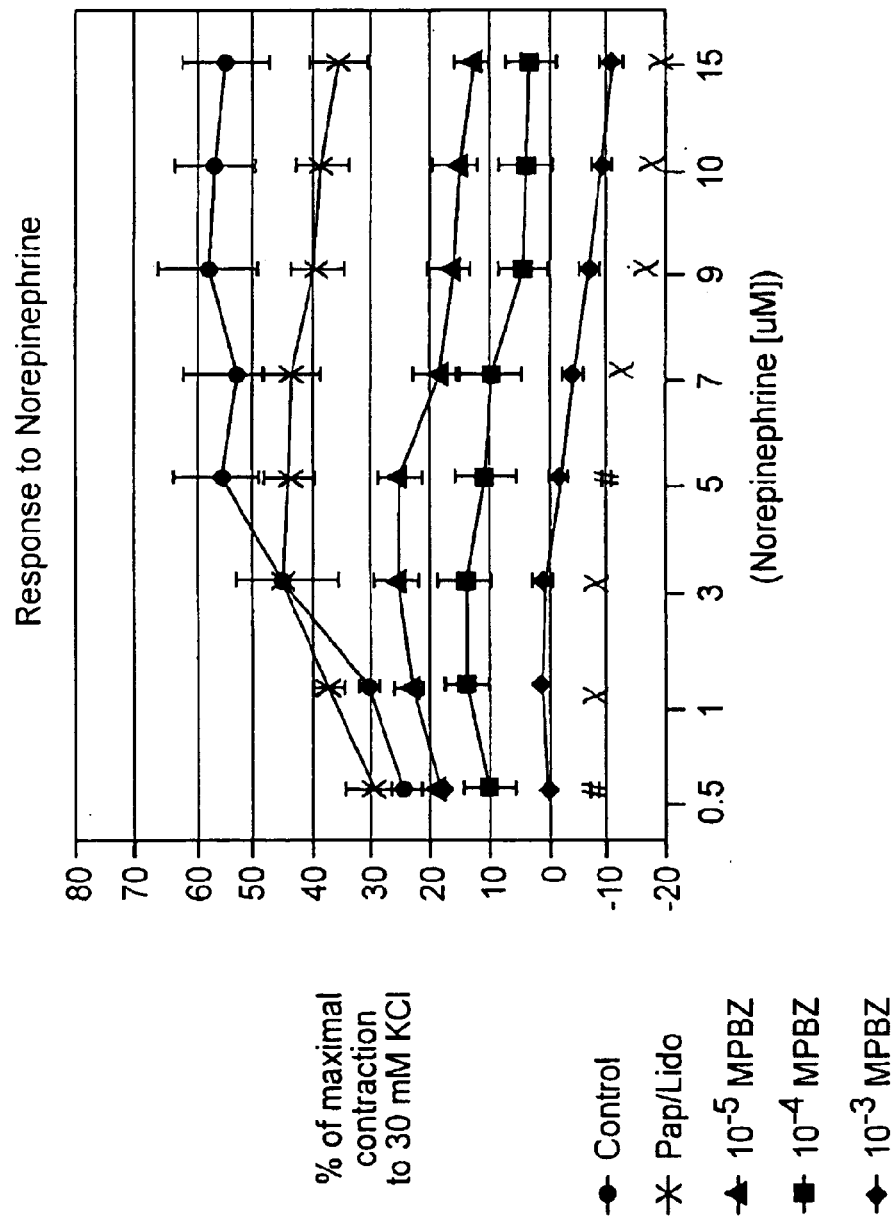
FIG. 5 depicts radial artery vasocontraction responses to increasing concentrations of norepinephrine, with or without pretreatment with three different concentrations of phenoxybenzamine (PBZ)

Incremental concentrations of norepinephrine also caused progressive vasoconstriction in control human RA segments (54.7±7.5% of maximal contraction to 30 mM KCl, FIG. 5). Soaking the RA in a combination of papaverine/lidocaine blood solution modestly but significantly attenuated this vasoconstriction response to 15 $\mu$M NE (35.6±5.1%, p=0.04). Although PBZ at 10 $\mu$M inhibited constriction to concentrations of NE greater than 7 $\mu$M, PBZ at 1000 $\mu$M completely inhibited constrictor responses across all concentrations of NE (FIG. 5). In summary, 1000 $\mu$M PBZ added to papaverine/lidocaine completely inhibits the vasoconstriction induced by PE and NE.

Figure 6:
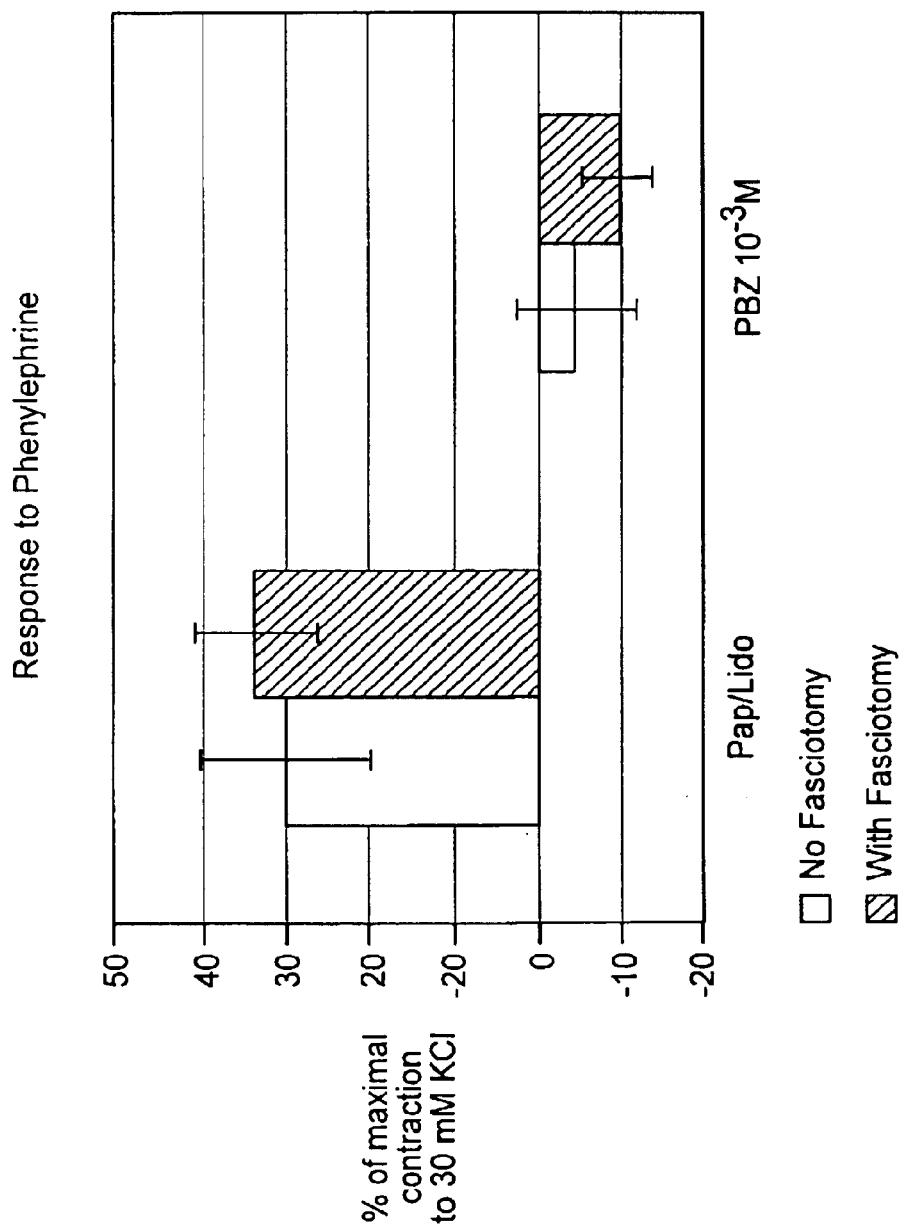
FIG. 6 depicts radial artery vasocontraction responses to 15 $\mu$M phenylephrine, with and without fasciotomy after treatment with $10^{-3}$ M phenoxybenzamine (PBZ) or papaverine/lidocaine (Pap/Lido)
Figure 7:
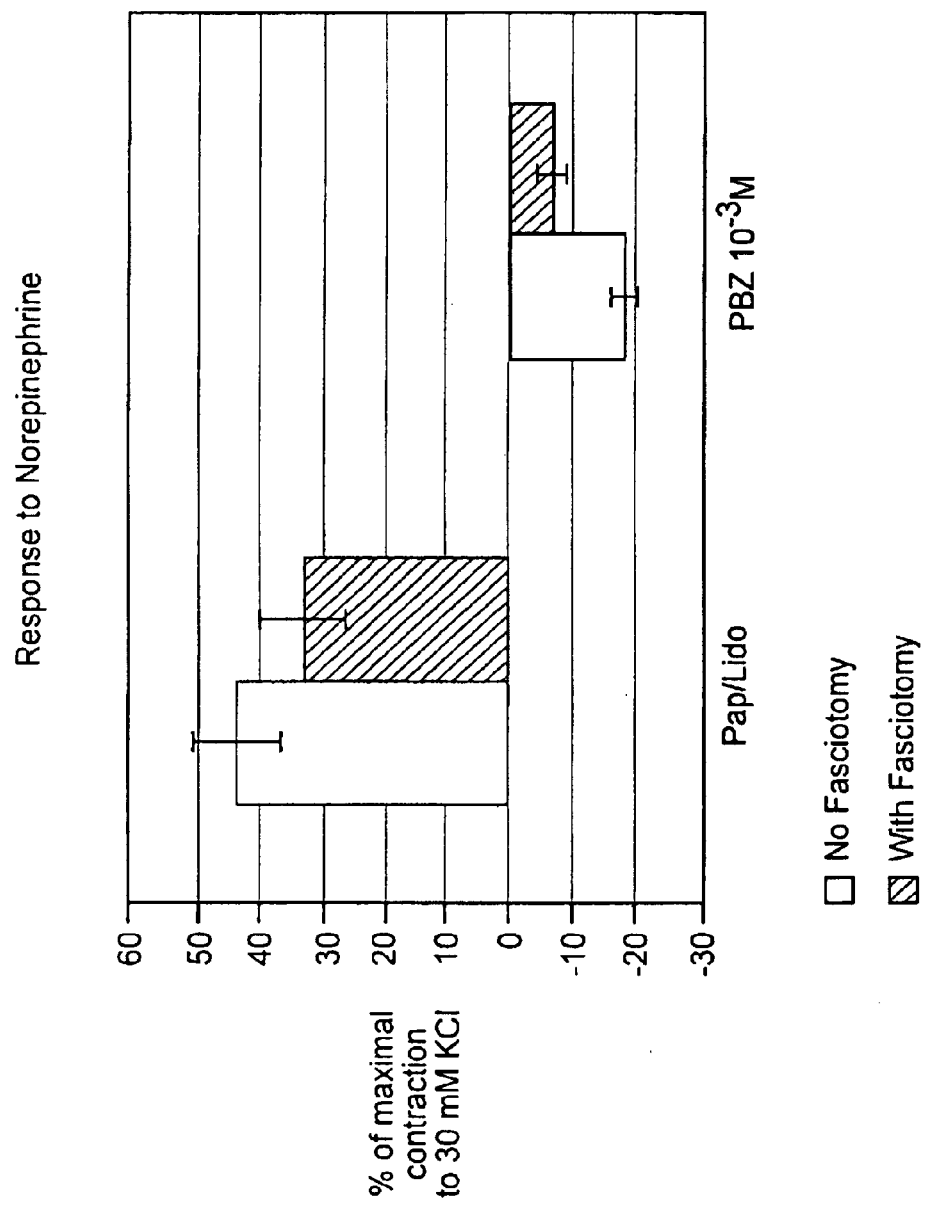
FIG. 7 depicts radial artery vasocontraction responses to 15 $\mu$M norepinephrine, with and without faxciotomy after treatment with $10^{-3}$ M phenoxybenzamine (PBZ) or papaverine/lidocaine (Pap/Lido)

The potential for fasciotomy at the time of RA harvest to facilitate exposure of the vessel to PBZ pretreatment was investigated. At the highest concentration of phenylephrine tested (15 $\mu$M), there was no significant difference between RA segments with fasciotomy and without fasciotomy with either papaverine/lidocaine treatment or PBZ treatment (1000 μM), FIG. 6. Similarly there was no benefit to fasciotomy with either papaverine/lidocaine pretreatment or PBZ pretreatment when vasoconstriction was achieved by norepinephrine (FIG. 7).

Figure 8:
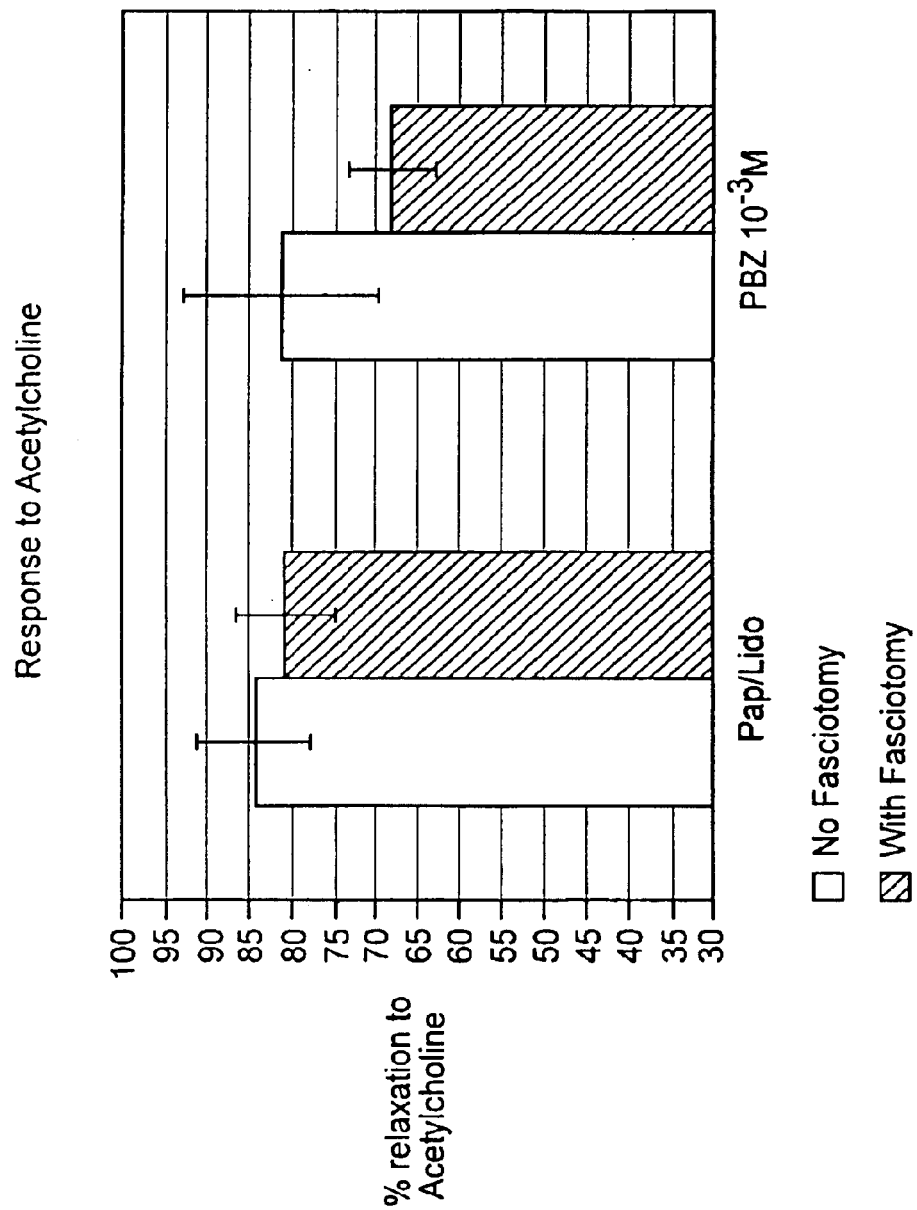
FIG. 8 depicts radial artery endothelial function expressed as percent relaxation to 12 $\mu$M acetylcholine, with and without fasciotomy after treatment with $10^{-3}$ M phenoxybenzamine (PBZ) or papavarine/lidocaine (Pap/Lido).

RA endothelial function was tested by quantifying the relaxation response to increasing concentrations of acetylcholine (ACh), a receptor dependent stimulator of nitric oxide synthase. Endothelial function was not significantly attenuated in RA segments in which a fasciotomy was performed (FIG. 8). In the segments treated with papaverine/lidocaine, those without fasciotomy demonstrated an 84.6±6.8% relaxation response to 12 μM ACh, and those with fasciotomy demonstrated an 80.7±5.7% relaxation response (p=NS). In the segments treated with 1000 μM PBZ in addition to intraoperative papaverine/lidocaine, those without fasciotomy demonstrated an 81.0±11.8% relaxation response to 12 μM ACh, suggesting no additional impairment of endothelial function compared to RA segments treated with papaverine/lidocaine alone. Those with fasciotomy and treated with PBZ/papaverine/lidocaine showed a trend toward reduced endothelial function, averaging a 67.6+5.2% relaxation response to ACh (p=0.33 compared to segments treated with PBZ/papaverine/lidocaine without fasciotomy, unpaired Student t-test).

Although comparable contractile responses to KCl over the 2, 24, and 48 hour period of observation suggested that the vascular smooth muscle was viable after prolonged storage of the radial artery segments, the viability of the endophelium was also a concern with prolonged storage. The endothelium contributes to the overall vascular tone by tonic release of autacoids such as nitric oxide among other vasoactive substances. In addition, any attenuation of function related to autacoid release by phenoxybenzamine or its diluents would be undesirable. Endothelial relaxation responses to all concentrations of acetylcholine were comparable with or without phenoxybenzamine treatment over the 48-hour storage period. With phenoxybenzamine treatment the maximum relaxation response to the highest concentration of acetylcholine at 2 hours was 61%±5% after 24 hours was 57%±6% and 30%±5% after 48 hours; these levels of relaxation responses are comparable to untreated control radial artery segments. These data suggest that treatment of the radial artery segments with phenoxybenzamine does not alter viability or function of the endothelium, but rather provides an attenuation or minimization of constriction (vasospasm or spasticity) in the radial artery segments.

Clinical outcomes in coronary artery surgery depend on the long-term as well as immediate patency and longevity of the grafts used. Although the radial artery is a morphologically ideal alternative bypass graft conduit reports of vasospasm and "string signs" postoperatively have dampened the enthusiasm for the vessel as a by-pass graft. The dominance of alpha adrenergic receptors in this conduit determines the robust contractive responses to circulating catecholamines as well as to perioperatively administered adrenergic pressor agents commonly used in the postoperative period. The current regimens used to counteract or prevent vasospasm in radial artery bypass conduits (papaverine, lidocaine, nitroglycerin, calcium-channel blockers) suffer either from a temporary effect limited to the immediate operative period or from side effects in the case of systemic administration of calcium-channel blockers. In addition, calcium-channel blockers have not been particularly effective in preventing postoperative vasospasm of radial artery grafts.

The present examples of this invention demonstrate that a time-period exposure treatment of about 5 to about 60 minutes, and preferably for approximately 30-minutes, of the radial segments with low concentrations of phenoxybenzamine in solution attenuates constrictor responses to both norepinephrine and phenylephrine shortly after treatment, with attenuation/minimization of adrenergically induced contraction for up to 48 hours after an approximate 30-minute treatment with phenoxybenzamine.

The use of the alpha-adrenergic blocking agent may be solubilized to reduce the incidence of angina and myocardial infarction by attenuating (minimizing) spasticity and vasospasm in the harvested and implanted blood vessel graft in an ex-vivo method for the pretreatment and implantation or transplantation (grafting) of blood vessel grafts, preferably arterial grafts, in a patient undergoing vascular surgery. In such a procedure, the blood vessel to be used as a graft or transplant is harvested. If an artery is chosen as the graft, the harvested artery may be selected from the group consisting of internal mammary (thoracic) arteries, gastroepiploic arteries, inferior epigastric arteries, radial arteries and any other artery designated for a vascular conduit as known in the art. The harvested artery may include the pedicle of the artery or may be skeletonized (i.e. no pedicle). The pedicle may optionally be modified by a fasciotomy or other surgical procedure in order to permit an increased exposed of the tissue of the aterial graft to the spasticity minimizing agent pretreatment solution. The harvested blood vessel is then soaked for a period of time, approximately about 5 to about 60 minutes in the spasticity minimizing agent pretreatment solution, for example the phenozybenzamine pretreatment solution, for example phenozybenzamine, at least one vasodilator agent and an anti-coagulating agent. The concentration of the spasticity minimizing agent, for example phenoxybenzamine, in the spasticity minimizing agent pretreatment solution ranges from about $10^{-6}$M to about $10^{-1}$M.

The spasticity minimizing agent pretreatment solution, for example the phenoxybenzamine pretreatment solution, may be alternatively injected intralumenally into either the harvested artery, or a companion vein that may empty into the harvested artery, as part of the soaking step. The soaking step may also include placing the harvested blood vessel, for example a harvested artery, and the spasticity minimizing agent pretreatment solution, into an enclosure capable of being sealed and pressurized, and subjecting the so-enclosed harvested blood vessel in the spasticity minimizing agent pretreatment solution to a pressure of about 0.01 to 100 mm Hg for a period of time to assist the penetration of the pretreatment solution, such as the phenozybenzamine pretreatment solution, into the harvested blood vessel. Optionally, this pressurizing step may be performed by clamping or otherwise closing one end of the harvested artery, or companion vein that may empty into the harvested artery, prior to being pressurized.

Alternatively, the use of the alpha-adrenergic blocking agent may be solubilized and used to reduce the incidence of angina and myocardial infarction by attenuating spasticity and vasospasm in the harvested and implanted arterial graft through an in-vivo method utilizing the internal thoracic artery as an conduit. Said method employs the use of the alpha-adrenergic blocking agent, such as phenoxybenzamine, whereby the alpha-adrenergic blocking agent is solubilized in physiologic solution and infused into the vascular conduit in vivo where one end of the conduit is intentionally obstructed during the procedure to prevent exit of the agent from the conduit into the systemic circulation.

Figure 2:
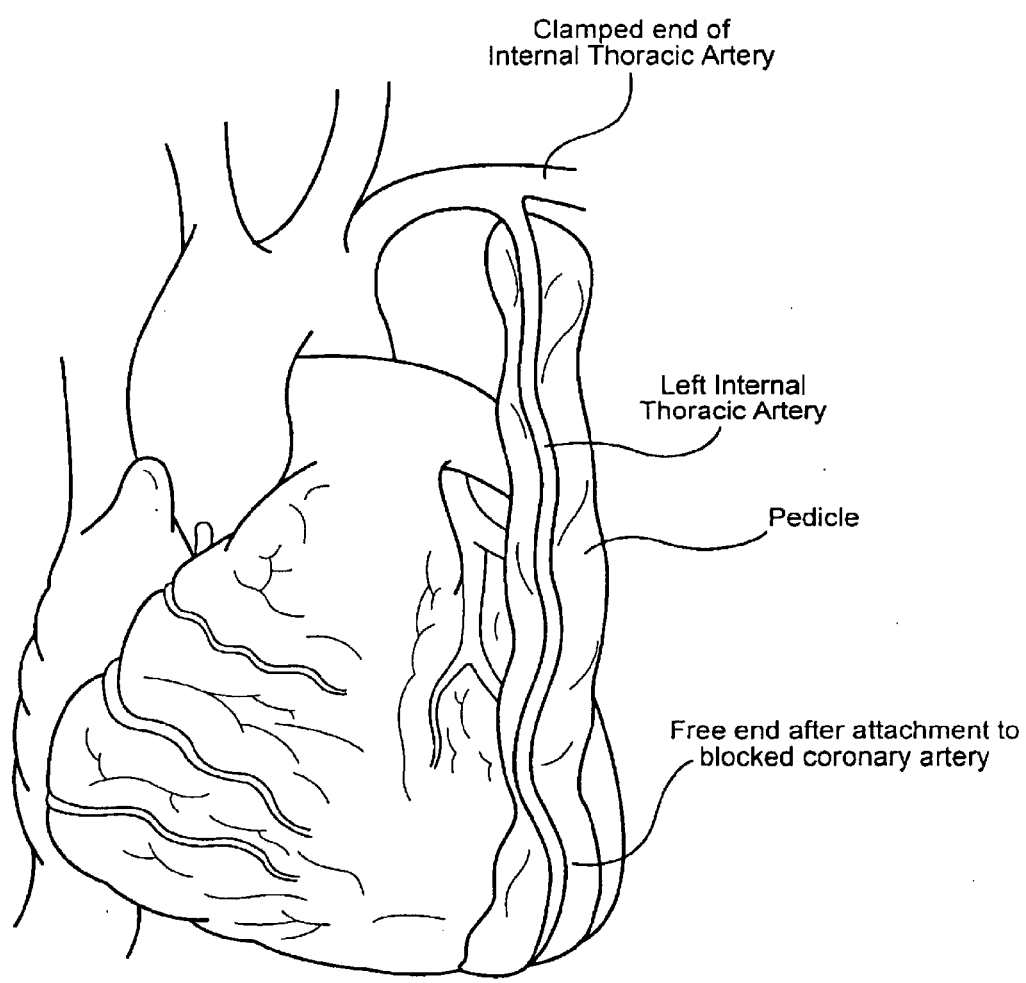
FIG. 2 depicts the internal thoracic artery and its location with respect to the heart with a notation depicting an alternative method, the in-vivo procedure, for clamping one end of the internal thoracic artery and infusing the artery, with pedicle as shown, with a spasticity agent minimizing solution (for example, a phenoxybenzamine solution), thus preventing entry of the solution into the systemic circulation.
Figure 3A:
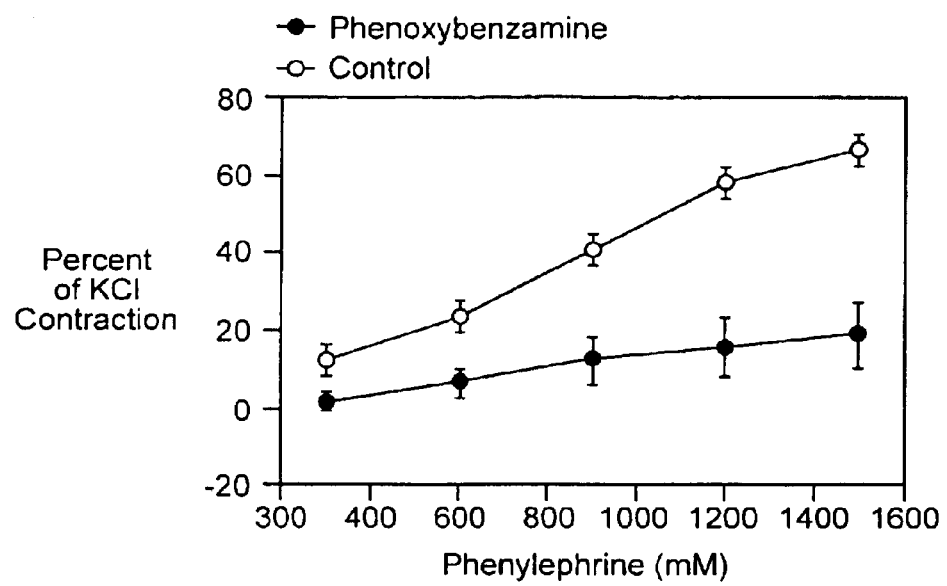
FIG. 3A depicts contractile responses of canine radial artery segments to phenylephrine after 2 hours of treatment with phenoxybenzamine.
Figure 3B:
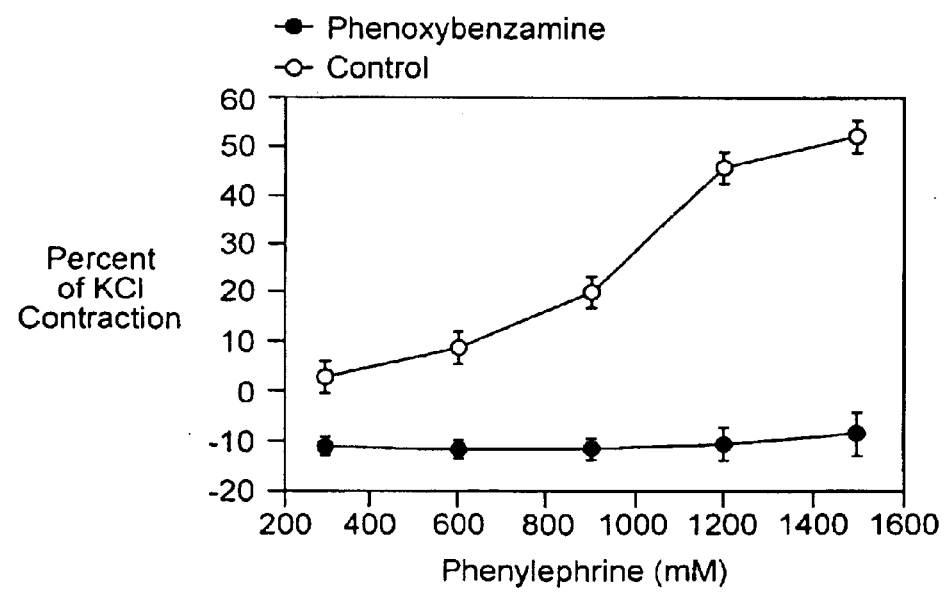
FIG. 3B depicts contractile responses of canine radial artery segments to phenylephrine after 24 hours of treatment with phenoxybenzamine.
Figure 3C:
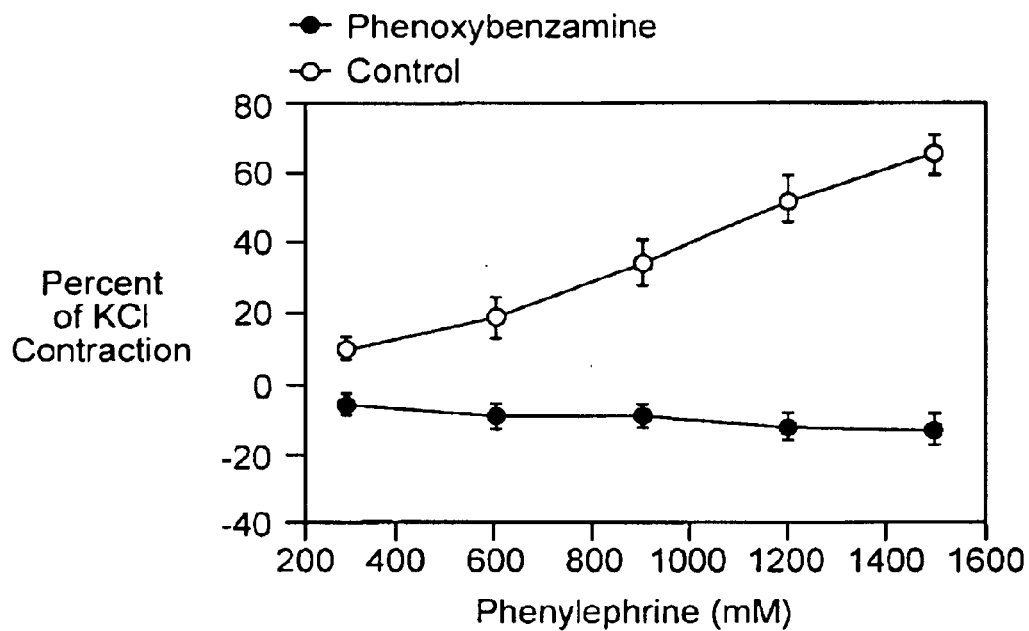
FIG. 3C depicts contractile responses of canine radial artery segments to phenylephrine after 48 hours of treatment with phenoxybenzamine.
Figure 3D:
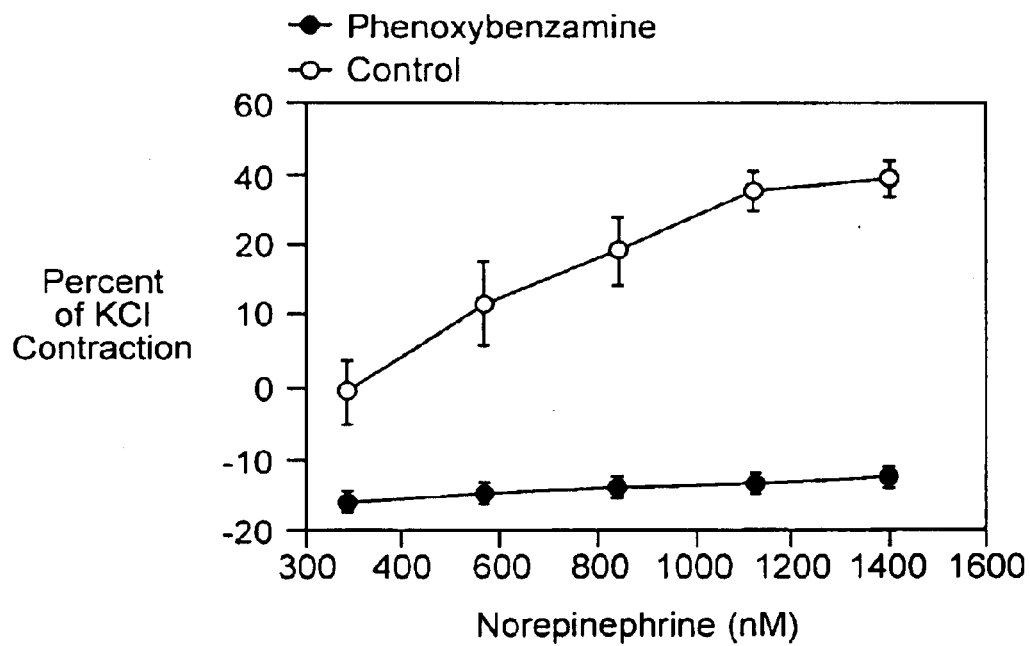
FIG. 3D depicts contractile responses of canine radial artery segments to norepinephrine after 2 hours of treatment with phenoxybenzamine.
Figure 3E:
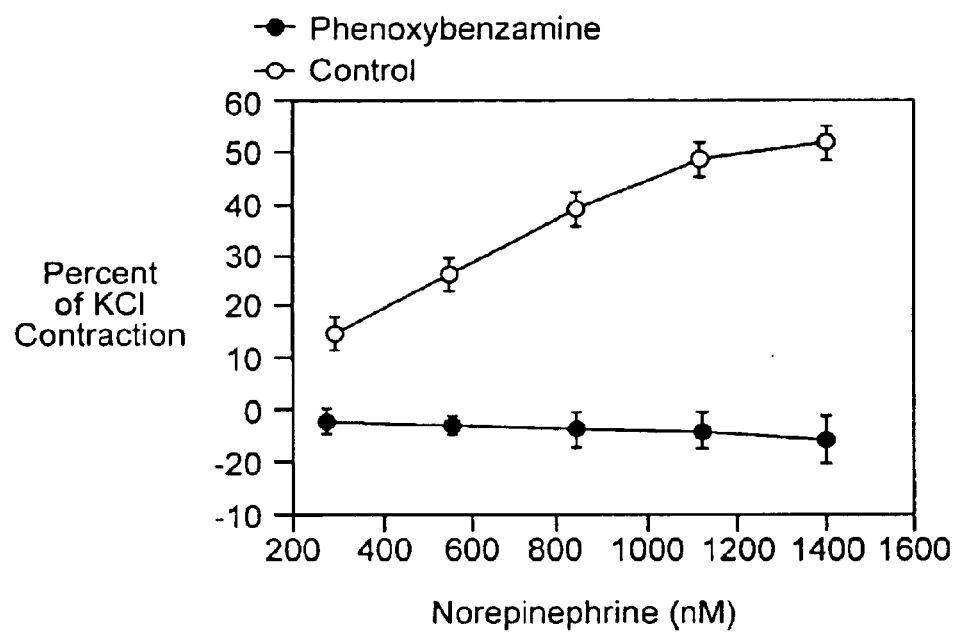
FIG. 3E depicts contractile responses of canine radial artery segments to norepinephrine after 24 hours of treatment with phenoxybenzamine.
Figure 3F:
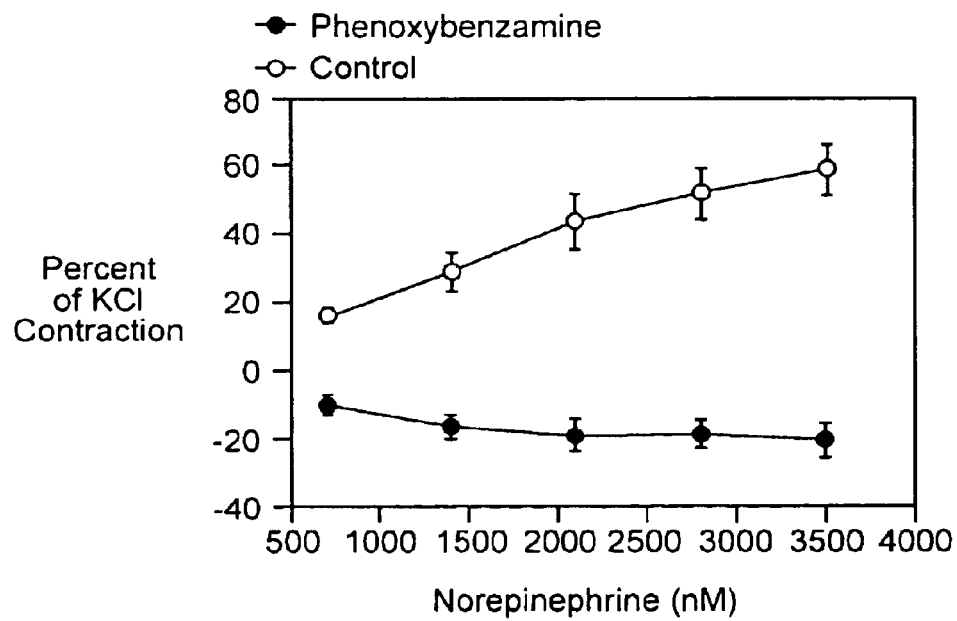
FIG. 3F depicts contractile responses of canine radial artery segments to norepinephrine after 48 hours of treatment with phenoxybenzamine.

See, for example, FIG. 2. Thus, the internal lumen of the internal thoracic artery (one end of the harvested artery conduit) is exposed to the phenoxybenzamine solution for a period of time, usually from about 5 minutes to about 60 minutes while the internal thoracic artery is still attached to the circulatory system of the patient. Following the exposure to the phenoxybenzamine or other alpha-adrenergic solution, the internal thoracic artery graft/conduit can be flushed with a physiologic solution and then prepared for attachment to the blocked coronary artery in accordance with known procedures. See, for example, FIG. 2. Blood flow to the coronary circulation through the now attached internal thoracic artery graft/conduit is re-established with a minimum of time between the harvesting of the internal thoracic artery graft/conduit and implantation as compared to the prior-art ex-vivo procedures.

Said internal thoracic artery conduit, being arterial in nature, is predisposed to vasospastic activity when exposed to inotropic pressor agents such as epinephrine, norepinephrine or other agents with alpha-adrenergic agonist activity, when said agents are utilized to maintain blood pressure during the perioperative period. Phenoxybenzamine, being an alpha-blocker, irreversibly binds to the alpha-receptor thereby preventing its stimulation during use of inotropic pressor agents during the perioperative period, after the conduit is attached to the blocked coronary artery and blood flow through the coronary circulation to heart muscle is re-established.

The in-vivo method of one embodiment of the present invention differs from that described for the ex-vivo radial artery conduit method (See, for example, FIG. 1) in that, in addition to the differences described above for in-vivo and ex-vivo procedures, the internal thoracic artery lacks the greater degree of vasospastic proclivity that is present in the radial artery conduit. Because of the higher degree of muscularity of the radial artery compared to the internal thoracic artery, the radial artery conduit has a greater risk of vasospasm either with or without the introduction of inotropic pressor agents to maintain blood pressure during the perioperative period. For this reason, radial artery use as a conduit for the coronary artery bypass procedure was even abandoned for a time.

With regard to the case of the internal thoracic artery, the degree of proclivity for vasospasm becomes a clinical issue only when inotropic pressor agents are used, as this artery does not tend to vasospasm unless stimulated by an exogenous pressor agent to do so. In the case of the radial artery conduit, the artery tends to spasm spontaneously due to its higher degree of muscularity and without the introduction of inotropic pressor agents. For this reason, the internal thoracic artery method is one of the prevention of angina and myocardial infarction in the coronary artery bypass graft peri-operative period that may result from use of exogenous inotropic pressor agents while the radial artery method is one of treatment of the proclivity for spontaneous, non-exogenously induced, vasospasm prior to coronary artery bypass graft. The time difference between the two methods, ex-vivo and in-vivo, as well as the differences mentioned above, may often be critical when performing a coronary bypass grafting procedure.

While the foregoing is directed to the preferred embodiments of the present invention, other and further embodiments of the invention may be devised without departing from the basic scope thereof, and the scope thereof is determined by the claims that follow.

What is claimed is:

1. A combination comprising: a formulation solution including
    a spasticity minimizing agent,
    an anti-coagulating agent and
    at least one vasodilatory agent, and
    a blood vessel graft suitable for use in coronary artery bypass grafting in contact with the solution
    wherein the formulation is effective to reduce vasoconstriction in the graft induced by inotropic agents for up to 48 hours,
    wherein the spasticity minimizing agent is selected from the group consisting of haloalkylamine alpha adrenergic blocking agents and
    wherein the at least one vasodilatory agent is selected from the group consisting of lidocaine, xylocaine, tetracaine, procaine, short term vasodilators, papaverine, adenosine, nitric oxide donor agents, calcium channel blocker agents, sodium channel blocker agents and adenosine regulating agents.

2. The formulation of claim 1 wherein said haloalkylamine alpha-adrenergic blocking agent is selected from the group consisting of phenoxybenzamine, isomers of phenoxybenzamine and tertiary amines of phenoxybenzamine.

3. The formulation of claim 1 wherein the spasticity minimizing agent is present in solution in a concentration of about $10^{-6}$M to about $10^{-1}$M, the anti-coagulating agent is present in a concentration sufficient to make activated clotting time greater than about 200 seconds.

4. The formulation of claim 1, wherein the anti-coagulating agent is selected from the group consisting of heparin, coumadin, ETDA, citrate, EGTA and other anti-coagulating agents that increase activated clotting time greater than about 200 seconds.

* * * * *